US010183121B2

(12) United States Patent
Cowe

(10) Patent No.: US 10,183,121 B2
(45) Date of Patent: Jan. 22, 2019

(54) INJECTION DEVICES

(71) Applicant: Owen Mumford Ltd., Oxford (GB)

(72) Inventor: Toby Cowe, Oxford (GB)

(73) Assignee: OWEN MUMFORD LIMITED, Oxford (GB)

(*) Notice: Subject to any disclaimer, the term of this patent is extended or adjusted under 35 U.S.C. 154(b) by 268 days.

(21) Appl. No.: 14/910,155

(22) PCT Filed: Aug. 5, 2014

(86) PCT No.: PCT/GB2014/052391
§ 371 (c)(1),
(2) Date: Feb. 4, 2016

(87) PCT Pub. No.: WO2015/019071
PCT Pub. Date: Feb. 12, 2015

(65) Prior Publication Data
US 2016/0193415 A1 Jul. 7, 2016

(30) Foreign Application Priority Data
Aug. 5, 2013 (GB) .................................. 1313982.9

(51) Int. Cl.
A61M 5/20 (2006.01)
A61M 5/315 (2006.01)

(52) U.S. Cl.
CPC ........ A61M 5/3157 (2013.01); A61M 5/2033 (2013.01); A61M 5/31511 (2013.01);
(Continued)

(58) Field of Classification Search
CPC .............. A61M 5/3157; A61M 5/2033; A61M 5/31511
See application file for complete search history.

(56) References Cited

U.S. PATENT DOCUMENTS 6,699,218 B2 * 3/2004 Flaherty ............ A61M 5/14248
604/131
9,186,458 B2 * 11/2015 Giambattista ....... A61M 5/2033
(Continued)

FOREIGN PATENT DOCUMENTS

CN 102245233 A 11/2011
GB 2488578 A 9/2012
(Continued)

OTHER PUBLICATIONS

International Search Report and Written Opinion of the International Searching Authority issued in PCT application PCT/GB2014/052391, dated Oct. 29, 2014, 12 pages.
(Continued)

Primary Examiner — Nathan R Price
Assistant Examiner — Dung T Ulsh
(74) Attorney, Agent, or Firm — Quarles & Brady LLP

(57) ABSTRACT

An injection device is disclosed which comprise a housing (10), a plunger (40) for expressing a medicament from a syringe (20) and an actuation mechanism (30). The actuation mechanism (30) is arranged in use to move the plunger (40) between a first rearward position and a second forward position to express a dose from the syringe (20). The injector device further comprises an injection activation sensor 51, arranged for example to provide an end of dose indication. The sensor 51 comprises an elongate flexible member (50). The flexible member (50) has a first end (52) connected to the plunger (40) or actuation mechanism (30) such that actuation motion of the injection device acts to move the elongate flexible member (50) relative to the housing. Movement of the elongate member (50) triggers a response to the injection such as an audible and/or tactile injection complete indication.

21 Claims, 6 Drawing Sheets

(52) U.S. Cl.
CPC . *A61M 2005/206* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 2011/0077599 A1 | 3/2011 | Wozencroft | |
| 2013/0041347 A1 | 2/2013 | Daniel | |
| 2014/0303556 A1* | 10/2014 | Travanty | A61M 5/2033 604/111 |
| 2015/0209505 A1* | 7/2015 | Hanson | A61M 5/1454 604/135 |
| 2016/0361503 A1* | 12/2016 | Bendek | A61M 5/3245 |
| 2017/0049968 A1* | 2/2017 | Choi | A61M 5/14 |

FOREIGN PATENT DOCUMENTS

| | | |
|---|---|---|
| GB | 2488579 A | 9/2012 |
| JP | 2012504008 | 2/2012 |
| JP | 2012511350 A | 5/2012 |
| WO | 2010/035056 A1 | 4/2010 |
| WO | 2010/035059 A1 | 4/2010 |
| WO | 2010/066592 A2 | 6/2010 |
| WO | 2013077800 A1 | 5/2013 |
| WO | 2013/178512 A1 | 12/2013 |

OTHER PUBLICATIONS

Search Report issued in British Patent Application No. GB 1313982. 9, searched Jan. 26, 2014, 1 page.
First Office Action issued in corresponding Chinese Patent Application No. 201480044256.0, dated Jun. 4, 2018, 19 pages.
Notification of Reasons for Refusal issued in corresponding Japanese Patent Application No. 2016-532732, dated May 8, 2018, 9 pages.

* cited by examiner

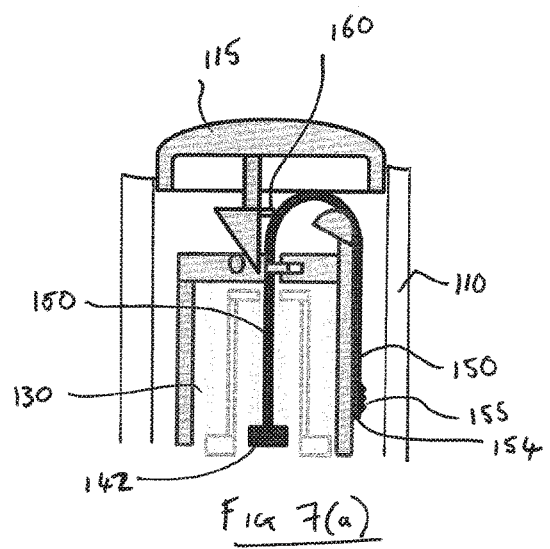
Fig 7(a)
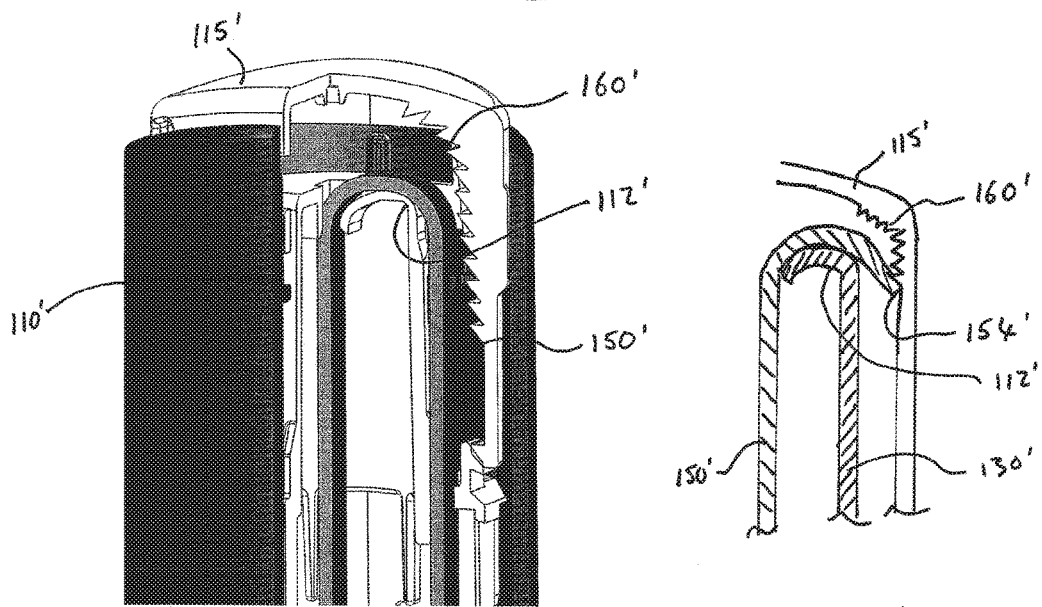
Fig 7(b)
Fig 7(c)

INJECTION DEVICES

CROSS-REFERENCE TO RELATED APPLICATIONS

This application represents the U.S. National Stage of International Application No. PCT/GB2014/052391, filed Aug. 5, 2014, which is based on, claims priority to, and incorporates herein by reference in its entirety, British Patent Application Serial No. GB 1313982.9, filed Aug. 5, 2013, and entitled, "Injection Devices."

FIELD OF THE INVENTION

This invention relates to injection devices including an activation indicator and in particular, but not exclusively to an auto injector device.

BACKGROUND OF THE INVENTION

Injection devices are used for the convenient administration of medicaments. For example, auto injectors may be used for providing a single metered dose of a medicament, such as Epinephrine, in an emergency or for providing regular metered doses of a medicament, such as insulin.

It is known to provide such injection devices with an activation indicator which provides one or more of a visual, tactile or audible indication of the firing of the injector actuation mechanism. In particular since the delivery of a desired dose of medicament may take a certain amount of time after the user activates the injector (particularly for example, with high viscosity drugs or small needle diameters) it is useful to provide an injection complete indication. The term "Injection Complete" (or "injection completion") is used to refer to a condition in which a satisfactory delivery of the medicament has been achieved.

It is desirable for auto injectors to be of a compact form so that they can be carried around and used unobtrusively (typically such auto injectors are provided in a pen injector type form). Further compact injectors may be simple to manufacture, assemble and use with consequent savings in manufacturing and assembly costs, and a lower environmental impact. Accordingly, any activation indicator provided within the injector must be of compact form and not significantly impact the overall size of the injection device.

Embodiments of the present invention are intended to address at least some of the abovementioned problems.

SUMMARY OF THE INVENTION

Accordingly, in one aspect, this invention provides an injection device comprising:
 a housing;
 a plunger arranged for expressing a medicament from a syringe;
 an actuation mechanism arranged in use to move the plunger between a first rearward position and a second forward position to express a dose from the syringe; wherein the injector device further comprises
  an injection activation sensor comprising
  an elongate flexible member having a first end connected to the plunger or actuation mechanism such that actuation motion of the injection device acts to move the elongate flexible member relative to the housing and
 wherein the movement of the elongate member triggers a response to the injection.

Typically, the injection activation sensor may be an injection completion sensor and as such the movement may trigger a response to the injection completion.

The injection activation sensor may, for example, trigger a further sequence within the injection device. For example, the sensor may trigger the retraction of a syringe after an injection. Alternatively, or additionally, the sensor could be used to trigger the movement or release of a needle shroud after injection. Advantageously, embodiments of the invention may allow the subsequent sequential action to be triggered by the actual satisfactory delivery of the medicament (since the sensor may for example sense movement of the plunger) rather than simply by the movement of the actuation device.

In some embodiments the response to the injection may be an indication to the user. Thus, the injection activation sensor may be an injection activation indicator. The response to the injection may be an injection complete indication.

According to another aspect the invention comprises an injection activation indicator for an injector comprising
 an elongate flexible member having a first end arranged to be connected in use to a plunger or actuation mechanism of the injector such that actuation motion of the injection device acts to move the elongate flexible member and said movement of the elongate member triggers an injection complete indication.

The elongate flexible member may be disposed within the housing, for example in a rearward portion of the housing. The motion of the plunger or actuation mechanism may draw the first end of the flexible member through the housing (for example forward within the housing).

The elongate flexible member may for example be a ribbon. Alternatively the flexible member may be a string. The flexible member may be formed from any convenient pliable material. Typically, the flexible member will be substantially inextensible. The flexible member may for example be paper or plastic.

The movement of the forward end of the flexible member may be arranged to unravel the flexible member from an initial position in which at least a portion of the flexible member follows a tortuous path. For example in the initial position the portion of the flexible member may be coiled. Alternatively, the flexible member may be folded (for example in a concertina manner) in the initial position.

The injection complete indication may be one or more of an audible, tactile or visual indication.

For example, a visual indication may be provided via a viewing window with which a portion of the flexible member may be aligned in its initial position. As the flexible member is drawn forwards the flexible member may move out of alignment with the viewing window. Alternatively, or additionally, as the flexible member is drawn forwards a second portion may be brought into alignment with the viewing window. For example the, or each, portion of the flexible member may be provided with a marking or colour to provide the visual indication.

An audible or tactile indication may be provided by the motion of the flexible member. For example the flexible member may have a textured surface to provide an audible and/or tactile "click" upon movement. In some embodiments at least a portion of the surface of the flexible member could be formed with a "saw-tooth" or ratchet type profile. A tooth (or pawl) may be provided associated with the housing for engaging the textured surface of the flexible member with the interaction between the tooth and textured surface provide an audible indication as the surfaces passes the tooth.

Alternatively or additionally, the rear end of the flexible member may engage, strike or flick a surface within the injector to provide an audible or tactile indication upon its unravelling. For example, the rear end of the flexible member may be arranged to strike a percussive surface at the end of the movement to provide an audible or tactile injection complete indication. In such an arrangement may, for example, be conveniently provided by providing a flexible member in the form of a coiled spring (which may for example be formed from a thin strip of metal).

The percussive surface may include at least a portion of the surface having a "saw-tooth" profile (to provide a series of audible and/or tactile "clicks" as the flexible member passes over the surface). The tip of the flexible member may engage the saw-tooth surface during movement of the plunger. Thus, the tip may act as a tooth or pawl.

In order to encourage the flexible member to contact a surface of the injector the flexible member may be curved or folded over a structure within the injector (for example a fixed part of the actuation mechanism or housing). As such, the structure may act as a fulcrum about which the flexible member pivots during movement. As the flexible member may have a selected degree of resilience the pivoting over the member may cause the end of the flexible member to splay (for example in a radially outward direction) into contact with a percussive surface.

In at least its initial position the flexible member may be threaded between an opposed pair of injection indicator elements. A gap or nip may be defined between the elements through which the flexible element is threaded in at least its initial position. Movement of the flexible member through the nip between the elements may trigger the injection complete indication.

The elements may be relatively moveable. The elements may be biased towards a closed position. The flexible member may be arranged to hold the injector elements out of contact (i.e. when it is positioned within the nip between the elements). The length of the flexible member may be selected such that the rear end of the flexible member exits the nip between the injection indicator elements upon completion of effective dose delivery. In order to allow for tolerances the flexible member may exit the nip slightly prior to the forward most position of the plunger or actuation mechanism.

The injection indicator elements may be arranged to provide a mechanical indication. For example the flexible member may click through the elements. Alternatively, the elements may be arranged to mechanically strike thereby providing an audible or tactile injection complete indication.

Alternatively or additionally, the injection indicators elements may comprise a pair of electrical contacts. Thus, the elements may form a switch which is triggered by the movement of the flexible member so as to provide an injection complete indication. The flexible member may act as an isolating insulator between the contacts when it its initial position. The electrical contacts may connect when the flexible member exits the nip between the elements.

Alternatively or additionally, the flexible member may comprise at least one contact. The, or each, contact may initially be provided on a portion of the flexible member which is position rearwardly relative to the indicator elements (for example on the portion of the flexible member follows a tortuous path) and may pass between the elements during activation such that a circuit is completed.

The, or each, contact may extend along the longitudinal direction of the flexible member. Such an arrangement may, for example, enable an electrical connection to be made and remain connected for a desired period of the movement of the flexible member. The flexible member may comprise at least two spaced apart contacts. The contacts may each extend parallel to the longitudinal direction of the flexible member. The contacts may be spaced apart in the transverse direction. A first contact may be arranged to provide an injection commencement indication and a second contact may be arranged to provide an injection complete indication. At least a portion of the first contact may be positioned forward of the second contact.

The forward end of the flexible member may be connected to the plunger. The plunger may be provided with an internal bore through which the forward end of the flexible member extends. The forward end of the flexible member may comprise a plug which is received within the bore and which may prevent rearward movement of the end relative to the plunger. Alternatively, the flexible member may be integrally formed onto the plunger by a number of manufacturing methods.

Whilst the invention has been described above, it extends to any inventive combination set out above, or in the following description or drawings.

BRIEF DESCRIPTION OF THE DRAWINGS

The invention may be performed in various ways, and embodiments thereof will now be described by way of example only, reference being made to the accompanying drawings, in which:

FIGS. 7a, 7b and 7c are a partial cross sectional representation of an alternate embodiment of the invention.

DETAILED DESCRIPTION OF EMBODIMENTS

Front as used herein will be understood to refer to the end of the injector assembly (or components thereof) which, in use, are closest to the delivery needle delivery end of the injector (i.e. the end which is pointed at the skin). Rear as used herein will be understood to refer to the end of the injector assembly (or components thereof) which, in use, are furthest from the delivery needle end of the injector (i.e. the end which is pointed away from the skin). Forward and rearward will, likewise, be understood to refer to the directions orientated towards the front and rear of the injector assembly. With respect to the flexible member forward and rearward will be understood to refer to the position of the portions when the member is extended regardless of the positioning of the elements when the flexible member is in a tortuous configuration.

For convenience the preferred embodiment is shown in an injector device of the type disclosed in the applicants co-pending International Patent Application No. PCT/GB2011/051950 (the contents of which is incorporated herein by reference). It will however be appreciated that the invention is not limited to such an arrangement and may be used in injectors having other actuation arrangements.

Figure 1:
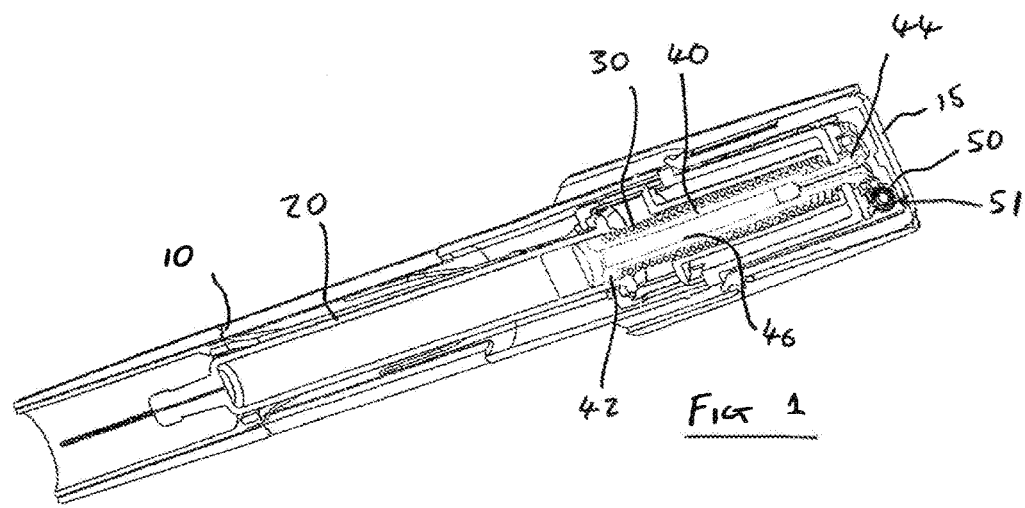
FIG. 1 is a cross sectional view of the first embodiment of an autoinjector in accordance with this invention in a ready to use configuration.

An injector device 1 according to an embodiment comprises a housing 10 having a generally elongate and cylindrical form within which is housed a syringe 20. The rear portion of housing 10 includes an actuation mechanism 30 which may be of any convenient form and is arranged to move a plunger 40 between a first, rearward, position as shown in FIG. 1 and a second, forward, position (shown for example in FIG. 4) such that the plunger may express a dose from the syringe 20. In the illustrated embodiment the actuation mechanism is of the type which initially moves the syringe forward from within the housing such that the needle of the syringe may automatically penetrate the skin and then subsequently continues to move the plunger relative to the syringe to express the entire dose of medicament from within the syringe. As mentioned above, the present invention is not limited to any particular actuation mechanism and it will, therefore, be appreciated that in other embodiments the actuation mechanism may be arranged to only partially move the plunger in response to the activation (and therefore the second position may be one in which the plunger has only moved partially along the syringe). It will also be appreciated that other injector arrangements are known in which the needle protrudes from the housing prior to firing such that it is manually inserted into the skin (and the syringe may be fixed relative to the housing).

Figure 2:
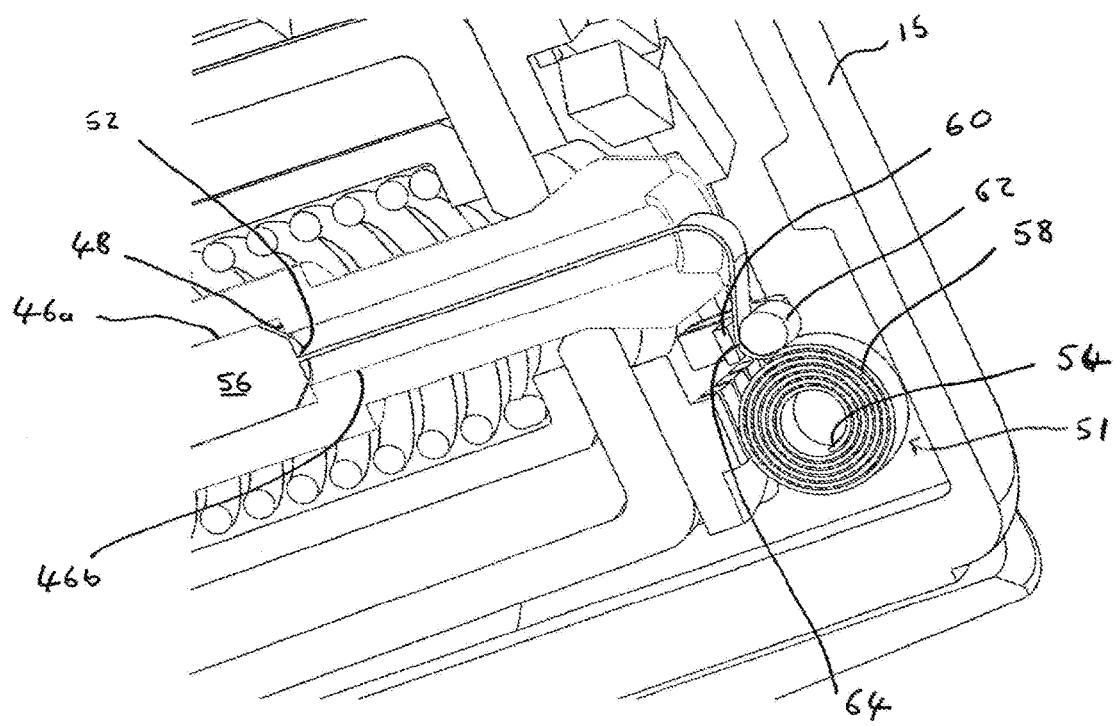
FIG. 2 is a detailed view of the rearward section of the autoinjector of FIG. 1.

In the preferred embodiment, the plunger 40 is provided with a bore 46 which extended from the head of the plunger 42 to the rear end of the plunger 44. As best seen in FIG. 2, a flexible member 50 of an injection activation sensor 51 is provided which has a forward end 52 which is connected to the plunger 40 via a plug 56 which is seated within the bore 46. The plug 56 is permanently attached to the forward end 52 of the flexible member 50 and is slidingly received within a forward portion 46a of the bore within the plunger 40. A rearward section of the bore 46b has a reduced internal diameter and a shoulder 48 is defined between the first 46a and second 46b portions of the bore. Thus, the plug 56 is prevented from moving rearwardly beyond the shoulder 48 and (as will be explained in further detail below) will be drawn forward upon forward movement of the plunger 40. It will be appreciated that in other embodiments the flexible member 50 may be attached to the plunger 40 by any suitable means. For example the flexible member 50 may be permanent attached to the plunger. For example, the plunger 40 and flexible member 50 may be co-moulded or plastic-welded.

Rearwardly of the plunger 40 the flexible member 50 is initially arranged to follow a tortuous path such that it is folded along its longitudinal length. This provides a compact initial arrangement of the flexible member 50 and preferably enables it to be fitted within the housing with little or no increase in size of the injector. In the embodiment of FIGS. 1 and 2 the rear portion of the flexible member 50 is arranged as a coil 58. In an alternative embodiment shown in FIG. 3 the tortuous portion may be folded in a concertina manner 58'. It will be appreciated any convenient shape may be selected for the tortuous portion depending upon the available space within the housing 10 (and taking into account the manner and direction in which the flexible member 50 will unravel during activation).

Figure 3:
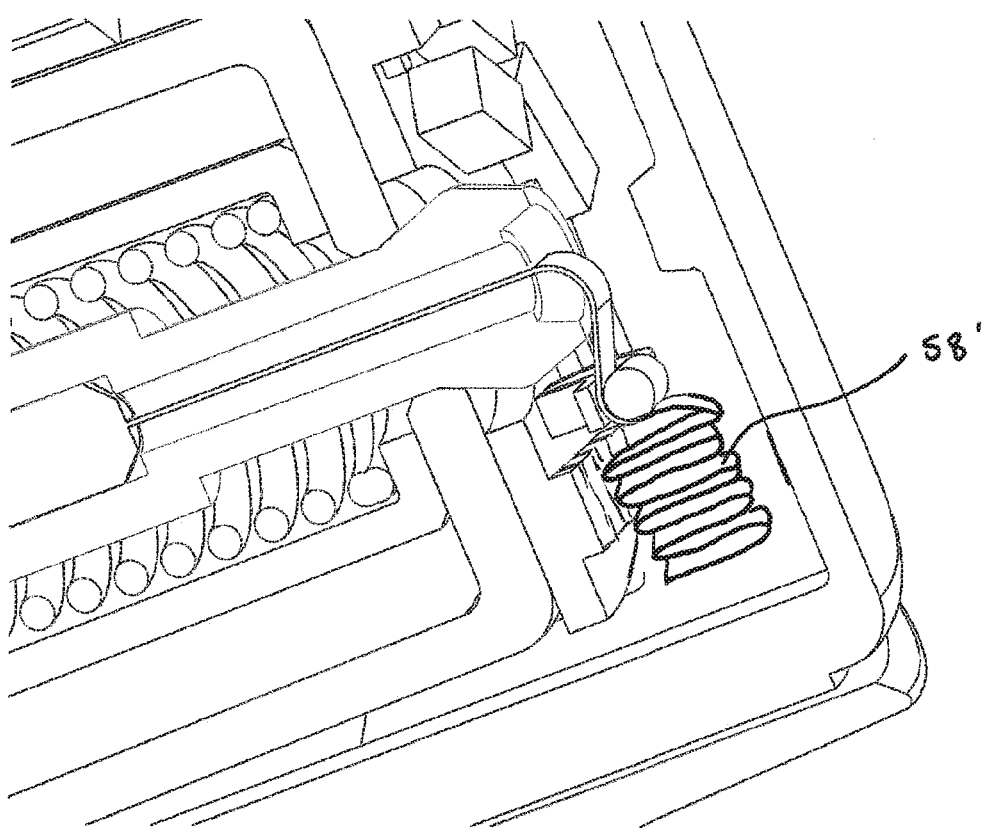
FIG. 3 is a detailed view of the rearward section of an autoinjector showing an alternative embodiment of the invention.

Between the plunger 40 and the coil 58 the flexible member is threaded through the nip 64 defined between two opposing indicator elements 60, 62. The indicator elements 60, 62 are resiliently biased towards a closed position (for example by being formed on resilient plastic members) and are held apart by the presence of the flexible member 50. In the illustrated embodiment the forward indicator element 60 has a generally planar profile and the upper indicator element 62 is provided with a rounded profile which helps to guide the flexible member 50 as it unravels from the coil 58. As will be described in further detail below, the indicator elements 60, 62 may comprise a pair of electronic contacts which in the initial position of FIGS. 1 to 3 are held apart (or insulated from one another) by the presence of the flexible member 50 within the nip 64.

Figure 4A:
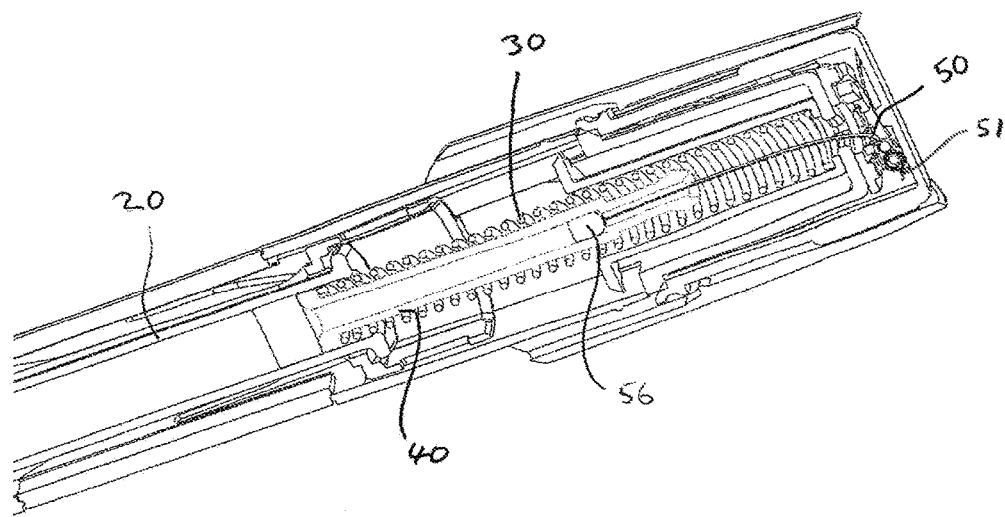
FIGS. 4(a) to (d) are cross sectional views of the autoinjector of FIGS. 1 and 2 showing the activation sequence.

Operation of the injection activation indicator will now be described with reference to FIGS. 4(a) to (d). FIG. 4(a) shows the injector device shortly after a user has depressed the activation trigger resulting in the release of the plunger 40 which is propelled forward by the spring of the actuation mechanism 30. Initially, the plunger acts to drive the syringe 20 forwards such that the needle may penetrate the skin but (due to the compressibility of the medicament within the syringe) the plunger does not initially move the piston of the syringe relative to the syringe body. As the plunger 40 moves forwardly, the plug 56 is captive within the bore 46 and results in the forward end 52 of the flexible member 50 being drawn forward with the plunger 40. As a result, it will be noted that in FIG. 4(a) the coil 58 has begun to unravel such that the flexible member 50 may extend along the axial direction of the injector device.

Figure 4B:
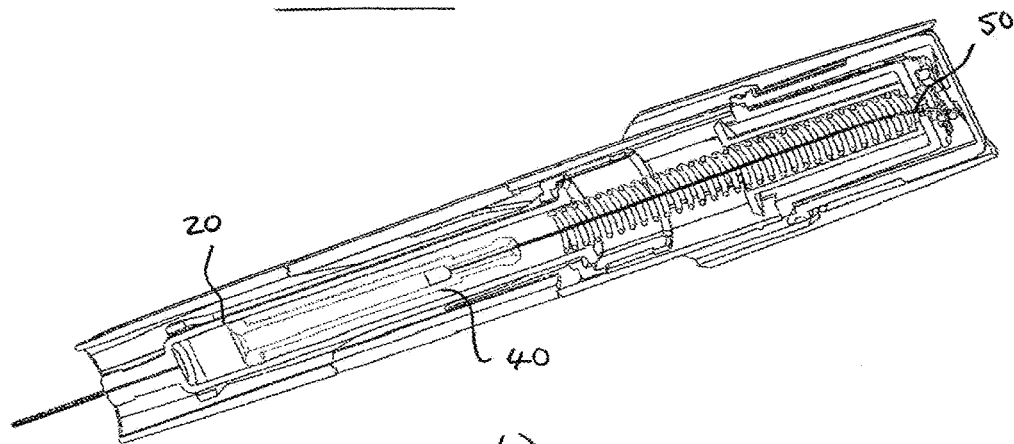

As shown in FIG. 4(b) once the syringe 20 reaches it forwardmost position the actuation mechanism 30 continues to drive the plunger 40 forwards such that it may dispense the medicament through the needle of the syringe 20. In the position shown in FIG. 4(b) the plunger is approaching its forwardmost position and as such the coil 58 has entirely unravelled and the rear end 54 is proximal to the indicator elements 60 and 62.

Figure 4C:
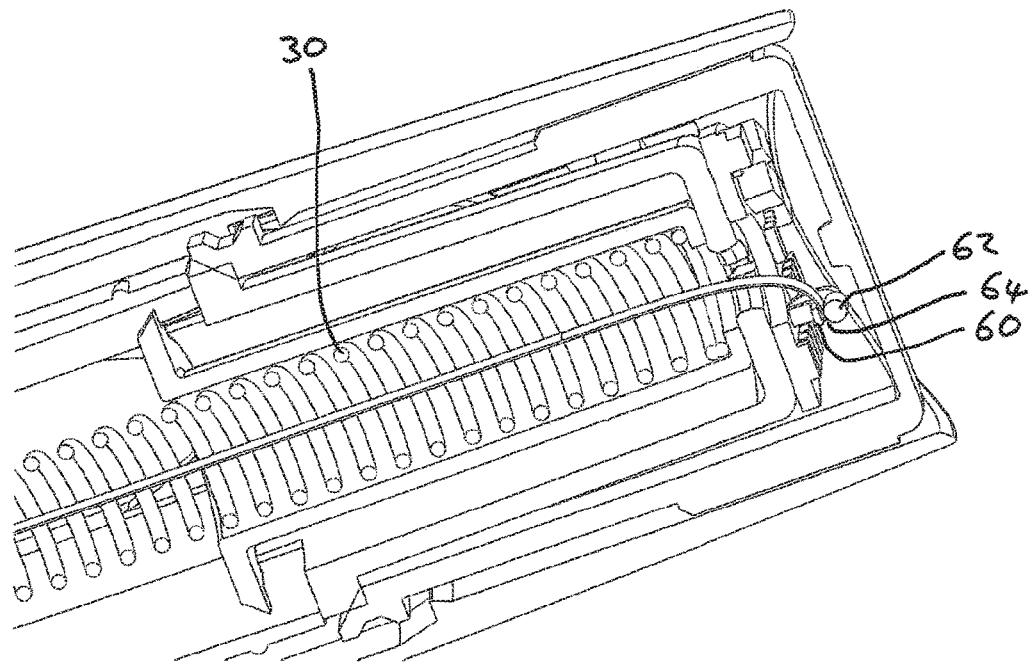
Figure 4D:
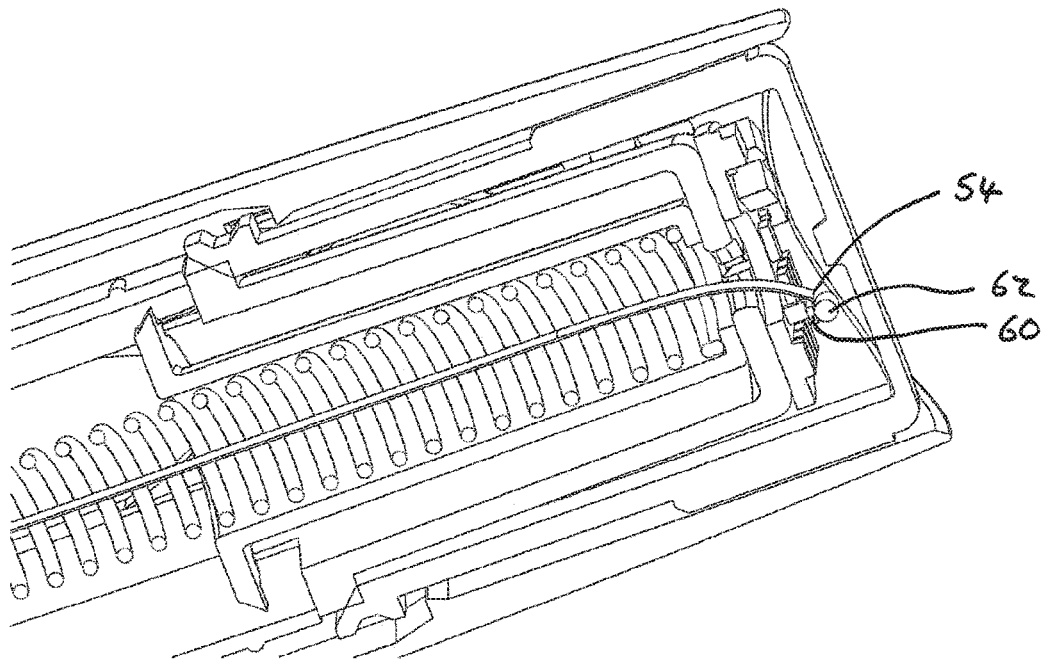

FIG. 4(c) shows the rear end of the injector device in greater detail in a similar position to that of FIG. 4(b). It will be noted that in FIG. 4(c) the rear end 54 of the flexible member 50 is positioned with the nip 64 between the indicator element 60 and 62. This position represents the configuration of the device with the plunger is in a forward position but has not yet completed delivery of a full dose. As shown in FIG. 4(d) the plunger continues its forward motion and draws the flexible member 50 further forward such that the end 54 exits the nip 64. Due to their resilient bias the indicator elements 60 and 62 close together upon removal of the flexible member 54 resulting in the completion of an electrical circuit. This connection is made slightly before the plunger 40 has completed its forward movement to allow for extremes of tolerance. Upon completion of the electrical circuit by the contact between the indicator elements 60 and 62 an audible, visual and/or tactile indication is provided (for example by means of a sounder, motor, speaker, LED, or piezoelectric actuator). Typically, the activation circuit is arranged to have a predetermined delay between the connection being made between the indicator element 62 and 60 and the issue of an injection complete indication of an indication to the end user to ensure that the medicament has been fully delivered dissipated and to compensate for the tolerance allowance in the length of the flexible member 50.

In some embodiments it may be desirable to provide multiple indications triggered by the extent of the movement of the plunger 40 or actuation mechanism 30. One convenient means for providing such multiple indications is to provide a plurality of electrical contacts on the flexible member 50 which are arranged to come into contact with the indicator elements 60 and 62 at a desired point during the activation of the injector device. Examples of a flexible member 50 arranged to provide such signals are shown in FIGS. 5 and 6.

Figure 5:
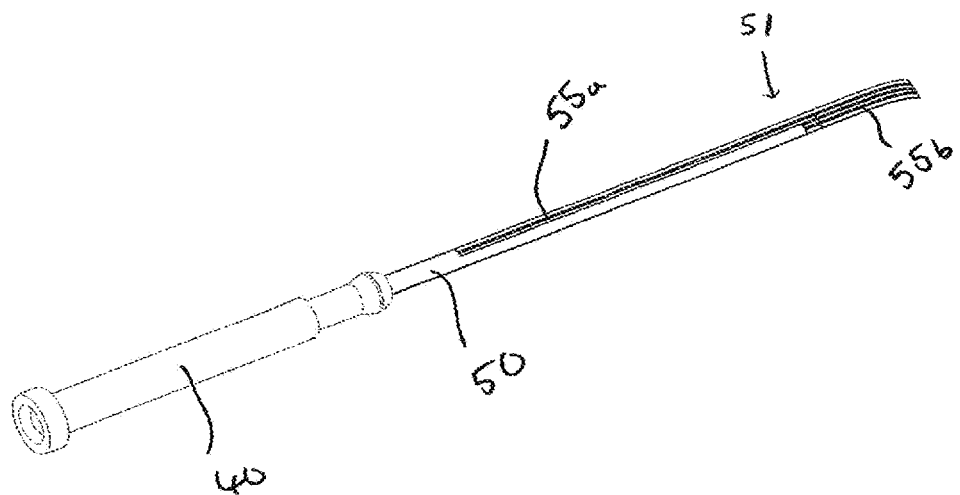
FIG. 5 is a plunger and flexible member for use in embodiments of the invention.

In FIG. 5 the flexible member includes a first 55a and second 55b contact strips which each extend parallel to the longitudinal direction of the flexible member 50 and which are spaced apart in the transverse direction. The contact strips each extend from the rearward end 54 of the flexible member 50 to a different forwardmost position. It will be appreciated that the forwardmost position of each strip 55 defines the point at which the contact strip will come into contact with the indicator elements 60 and 62. Thus, the contract strips allow easy adjustment of the point during the actuation process of the injector at which the indication is activated. In the illustrated example the first contact strip 55a would be arranged to initiate a low power mode on an indicator for example, an LED within the injector device (for example an indicator mounted to or within the plunger and visible through the housing) to provide the user with an indication that administration of an injection has commenced. The second contact strip 55b comes into the contact to make a secondary circuit as the actuation mechanism reaches it forwardmost position. Thus, the second strip 55b may switch the LED to a second state for example to a high power mode or to a pulsing mode and may also initiate a secondary indication of completion of the injection (for example a tactile and/or audible indication). As in earlier embodiments, there may typically be a small delay between the second contract strip 55b being made to ensure full drug delivery and dissipation before the user is provided the injection complete indication.

Figure 6:
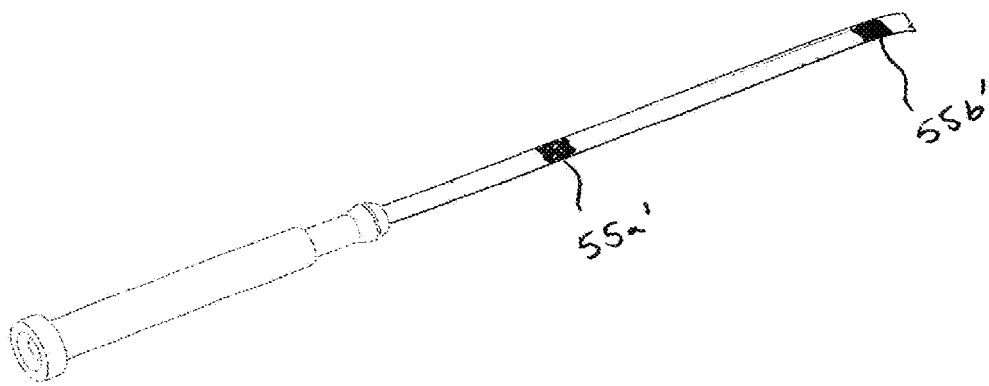
FIG. 6 is an alternative plunger and flexible member for use in embodiments of the invention.

FIG. 6 shows an alternative arrangement to that of FIG. 5 in which the spaced apart contact 55a' and 55b' provided on the flexible member 50' are spaced apart along the longitudinal direction of the flexible member and extend only locally in the longitudinal direction. In such an embodiment, an electrical indicator circuit may be provided which provides a first indication in response to the first connection being made (when contact 55a' passes through the indicator elements 60 and 62) and to display a second (and preferably distinct) indication when the second contact 55b' is aligned with the indicator elements 60 and 62.

Alternate embodiments of the invention are illustrated in FIGS. 7a to 7c. In each of these embodiments the elongate flexible member 150 extends to the head 142 of the plunger 140 and effectively replaces the stem of the plunger. At least the forward section of the elongate flexible member 150 is held under tension by the actuation mechanism 130 (which includes a spring). The skilled person will appreciate that in such an arrangement flexible elongate member will initially be held by a latch which is releasable in use by the movement of the activation trigger 115 so as to enable the spring of the actuation mechanism 130 to drive the plunger 140 forwards (and that the particular arrangement of such a latch is not an essential feature of the invention).

In the embodiment of FIG. 7a, the flexible elongate member 150 is provided with a textured surface in the form of a saw tooth profiled section 155 at, or proximal to, its rear end 154. A pawl 160 in the form of a resilient finger is provided as an indicator element. The pawl is associated with the trigger 115 (but could be otherwise associated with the housing 110) such that the plunger 140 and elongate member 150 move relative to the pawl 160 during activation of the device. The pawl 160 is positioned so as to engage the elongate flexible member 150 as the elongate flexible member moves forwardly during activation. The length of the elongate flexible member 150 and the position of the saw tooth section 155 are selected such that when the plunger approaches the delivery complete position the pawl 160 will come into contact with the saw tooth profile section 155. The pawl 160 will then be deflected across each tooth to provide an audible (and optionally tactile) click.

FIGS. 7b and 7c illustrate a variation of the embodiment of FIG. 7a, in which the indicator element 160' is provided as a saw-toothed surface formed on a portion of an interior surface of the trigger 115' (or other part of the housing 110'). In this embodiment the tip at the end 154' of the elongate flexible member 150' acts, in effect, as a pawl which moves across the saw tooth surface 160' during actuation. As seen in FIG. 7b, initially the elongate flexible member 150' is arranged in a configuration where it is folded over a rearward surface of a structure 112' formed on the interior of the housing (in the example by part of the latch of the actuation mechanism 130') so that it has a substantially U-shaped profile within the housing. During activation the structure 112' provides a fulcrum about which the elongate flexible member 150' folds as it is dragged forward with the plunger movement.

As shown in FIG. 7c, as the plunger reaches the delivery complete position the length of the elongate flexible member 150 is such that the end 154' of the elongate flexible member 150' will come into alignment with the surface 160'. The end 154' will splay outwardly towards the surface 160' due to the flexing over the fulcrum 112' and the resilience of the elongate flexible member 150'. Thus, the tip of the end 154' will engage the teeth of the saw tooth surface 160' and will be deflected across each tooth to provide an audible (and optionally tactile) click.

Although the invention has been described above with reference to the preferred embodiments, it will be appreciated that various changes or modifications may be made without departing from the scope of the invention as defined in the appended claims. In some embodiments the device may be a single use device and, for example, the syringe may be integrally formed with the housing.

Further, as mentioned above, the skilled person will appreciate that there may be additional sequences in the operation of an injector which it would be desirable to trigger in response to the successful delivery of a dose of medicament. Thus, the mechanical or electrical detection of the movement of the flexible member provided by embodiments of the invention may be utilised to trigger other sequences in addition or as an alternative to an injection complete indication sequence. For example, the flexible member may be utilised to initiate the commencement of a retraction sequence for the syringe, or to initiate the release of a shroud to cover the exposed needle.

The invention claimed is:
1. An injection device, comprising:
  a housing;
  a plunger for expressing a medicament from a syringe;
  an actuation mechanism arranged in use to move the plunger between a first rearward position and a second forward position to express a dose from the syringe; and
  an injection activation sensor including an elongate flexible member having a forward end connected to the plunger or actuation mechanism such that an actuation motion of the injection device acts to move the elongate flexible member relative to the housing, and wherein a movement of the elongate flexible member triggers a response to the injection device,
  wherein the elongate flexible member is threaded between an opposed pair of elements and a movement of the elongate flexible member through a nip between the elements triggers the response to an injection delivered by the injection device, wherein the elements are biased towards a closed position and wherein the elongate flexible member holds the elements out of contact, and wherein a length of the elongate flexible member is such that a rear end of the elongate flexible member exits the nip between the elements upon completion of effective dose delivery.

2. The injection device as claimed in claim 1, wherein the elongate flexible member triggers an injection completion indication.

3. The injection device as claimed in claim 1, wherein movement of the forward end of the elongate flexible member is arranged to unravel the elongate flexible member from an initial position in which at least a portion of the elongate flexible member follows a tortuous path.

4. The injection device as claimed in claim 3, wherein in the initial position, the portion of the elongate flexible member is coiled.

5. The injection device as claimed in claim 1, wherein a rear end of the elongate flexible member is arranged to strike or engage a percussive surface at the end of the movement to provide an audible or tactile injection complete indication.

6. The injection device as claimed in claim 1, wherein the opposed pair of elements are arranged to mechanically strike thereby providing an audible or tactile injection complete indication.

7. The injection device as claimed in claim 1 wherein the opposed pair of elements comprise a pair of electrical contacts.

8. The injection device as claimed in claim 7, wherein the elongate flexible member comprises at least one contact.

9. The injection device as claimed in claim 7, wherein the elongate flexible member comprises at least two spaced apart contacts.

10. The injection device as claimed in claim 9, wherein the contacts extend parallel to a longitudinal direction of the elongate flexible member.

11. The injection device as claimed in claim 9, wherein the contacts are spaced apart in a transverse direction.

12. The injection device as claimed in claim 9, wherein a first one of said contacts is arranged to provide an injection commencement indication and a second contact is arranged to provide an injection complete indication.

13. The injection device as claimed in claim 12, wherein at least a portion of the first contact is positioned forward of the second contact.

14. The injection device as claimed in claim 1, wherein the forward end of the elongate flexible member is connected to the plunger.

15. The injection device as claimed in claim 14, wherein the plunger is provided with an internal bore through which the forward end of the elongate flexible member extends.

16. The injection device as claimed in claim 15, wherein the forward end of the elongate flexible member comprises a plug which is received within the internal bore and which prevents rearward movement of the forward end relative to the plunger.

17. The injection device as claimed in claim 1, wherein at least one of the elongate flexible member and surface associated with the housing is provided with a toothed profile surface and the other of the elongate flexible member and surface forms a pawl which engages the surface to provide an audible or tactile injection complete indication.

18. The injection device as claimed in claim 17, wherein the toothed profile surface is provided on the elongate flexible member and the pawl comprises a resilient member associated with the housing and fixed relative to the elongate flexible member.

19. The injection device as claimed in claim 17, wherein the toothed profile is provided on an interior surface of, or associated with, the housing and wherein a tip of the elongate flexible member acts as the pawl which engages to toothed profile.

20. An injection device, comprising:
a housing;
a plunger for expressing a medicament from a syringe;
an actuation mechanism arranged in use to move the plunger between a first rearward position and a second forward position to express a dose from the syringe; and
an injection activation sensor including an elongate flexible member having a forward end connected to the plunger or actuation mechanism such that an actuation motion of the injection device acts to move the elongate flexible member relative to the housing and wherein a movement of the elongate flexible member triggers a response to an injection delivered by the injection device,
wherein the elongate flexible member is threaded between an opposed pair of elements and a movement of the elongate flexible member through a nip between the elements triggers the response to the injection device,
wherein the elements are biased towards a closed position and wherein the elongate flexible member holds the elements out of contact, and
wherein the elements are arranged to mechanically strike thereby providing an audible or tactile injection complete indication.

21. An injection device, comprising:
a housing;
a plunger for expressing a medicament from a syringe;
an actuation mechanism arranged in use to move the plunger between a first rearward position and a second forward position to express a dose from the syringe; and
an injection activation sensor including an elongate flexible member having a rearward end and a forward end connected to the plunger or actuation mechanism such that an actuation motion of the injection device acts to move the elongate flexible member relative to the housing and wherein a movement of the elongate flexible member triggers a response to an injection delivered by the injection device,
wherein the elongate flexible member is threaded between an opposed pair of transversely spaced apart electrical contacts and a movement of the elongate flexible member through a nip between the electrical contacts triggers the response to the injection device, and
wherein the elongate flexible member comprises at least two spaced apart contacts and wherein the contacts are spaced apart in a transverse direction and the contacts each extend from the rearward end of the elongate flexible member to a different forwardmost position.

* * * * *